United States Patent
Liao

(10) Patent No.: US 12,293,520 B2
(45) Date of Patent: May 6, 2025

(54) PORTRAIT IMAGE PROCESSING METHOD AND PORTRAIT IMAGE PROCESSING DEVICE

(71) Applicant: PixArt Imaging Inc., Hsin-Chu (TW)

(72) Inventor: Yuan-Hsin Liao, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 393 days.

(21) Appl. No.: 17/868,803

(22) Filed: Jul. 20, 2022

(65) Prior Publication Data

US 2024/0029261 A1 Jan. 25, 2024

(51) Int. Cl.
*G06T 7/11* (2017.01)
*A61B 5/00* (2006.01)
*G06V 40/16* (2022.01)

(52) U.S. Cl.
CPC .............. *G06T 7/11* (2017.01); *A61B 5/0077* (2013.01); *G06V 40/161* (2022.01); *G06T 2207/30201* (2013.01)

(58) Field of Classification Search
CPC ... G06T 7/11; G06T 2207/30201; G06T 5/00; G06T 11/00; G06T 2207/20201; G06T 7/0012; G06T 2207/30104; A61B 5/0077; A61B 5/0295; A61B 5/681; A61B 5/026; A61B 5/72; G06V 40/161; G06V 40/164
See application file for complete search history.

(56) References Cited

U.S. PATENT DOCUMENTS

| 2019/0175029 A1* | 6/2019 | Kumar .................. A61B 5/7246 |
| 2021/0386383 A1* | 12/2021 | McDuff ..................... G06T 5/50 |
| 2021/0398337 A1* | 12/2021 | McDuff .................. G06T 13/40 |
| 2022/0265150 A1* | 8/2022 | De Haan ............ A61B 5/14551 |

OTHER PUBLICATIONS

Kumar, Mayank, et al. "PulseCam: a camera-based, motion-robust and highly sensitive blood perfusion imaging modality." Scientific reports 10.1 (2020): 4825 (Year: 2020).*
Wang, Wenjin, et al. "Amplitude-selective filtering for remote-PPG." Biomedical optics express 8.3 (2017): 1965-1980. (Year: 2017).*

* cited by examiner

*Primary Examiner* — Oneal R Mistry
*Assistant Examiner* — Jongbong Nah
(74) *Attorney, Agent, or Firm* — Winston Hsu

(57) ABSTRACT

A portrait image processing method, applying to a portrait image processing device, comprising: (a) acquiring a BVP (Blood Volume Pulse) signal of a user; (b) acquiring blood flow distribution of a specific portion of a user; (c) capturing an image of a specific portion of the user; and (d) adjusting the image of the specific portion according to the BVP signal and the blood flow distribution. A portrait image processing device, which comprises a camera and a processing circuit, is also disclosed. The processing circuit can acquire BVP signals from an image captured by the camera or from a PPG sensor.

16 Claims, 8 Drawing Sheets

PORTRAIT IMAGE PROCESSING METHOD AND PORTRAIT IMAGE PROCESSING DEVICE

BACKGROUND OF THE INVENTION

1. Field of the Invention

The present invention relates to a portrait image processing method and a portrait image processing device, and particularly relate to a portrait image processing method and a portrait image processing device which can adjust a portrait image according to a BVP (Blood Volume Pulse) signal of a user.

2. Description of the Prior Art

In recent years, portrait filters become more and more popular. Many influencers use portrait filters while making a video or making live broadcasting, to make they look more handsome or beautiful. However, the conventional portrait filter always directly change the parameters of the portrait images of the user but does not consider the real condition of user's physiological parameters. Therefore, the adjusted portrait image may be less realistic.

SUMMARY OF THE INVENTION

One objective of the present invention is to provide a portrait image processing method which can adjust a portrait image in a proper manner.

Another objective of the present invention is to provide a portrait image processing device which can adjust a portrait image in a proper manner.

One embodiment of the present invention provides a portrait image processing method, applying to a portrait image processing device, comprising: (a) sensing a BVP (Blood Volume Pulse) signal of a user; (b) acquiring blood flow distribution of a specific portion of a user; (c) capturing an image of a specific portion of the user; and (d) adjusting the image of the specific portion according to the BVP signal and the blood flow distribution.

Another embodiment of the present invention provides a portrait image processing device, comprising: a camera, configured to capture an image of a specific portion of a user; and a processing circuit; wherein the processing circuit is configured to perform following steps: (a) acquiring a BVP (Blood Volume Pulse) signal of the user; (b) acquiring blood flow distribution of the specific portion; and (c) adjusting the image of the specific portion according to the BVP signal and the blood flow distribution.

In view of above-mentioned embodiments, the parameters of the portrait images of the user can be adjusted based on BVP signals, thus the adjusted portrait image may be more realistic or more vivid.

These and other objectives of the present invention will no doubt become obvious to those of ordinary skill in the art after reading the following detailed description of the preferred embodiment that is illustrated in the various figures and drawings.

DETAILED DESCRIPTION

Different embodiments are provided in following descriptions to explain the concept of the present invention. Please note, the components of each embodiment can be implemented by hardware (e.g. circuit, device, and apparatus) or hardware with software (e.g. a processor installed with at least one program). Besides, the components of each embodiment can be separated to more components or be integrated to fewer components. Additionally, the term "first", "second", "third" in following descriptions are only for explaining different components or different steps, but do not mean the sequence thereof. Further, in following embodiments, a face of a user is taken as an example. However, the concepts of the present invention can be provided to any other specific portion of a user. For example, the concepts of the present can be applied to a chest, an abdomen, a hand or a neck of a user.

Additionally, in following embodiments, the term "image" can mean a single still image or a video which contains a plurality of images. In following examples, a real time video is taken as example, this the real time video is automatically adjusted immediately after being captured by a camera. However, the following adjusting steps can be performed after the still image or the video is captured and recorded.

Figure 1:
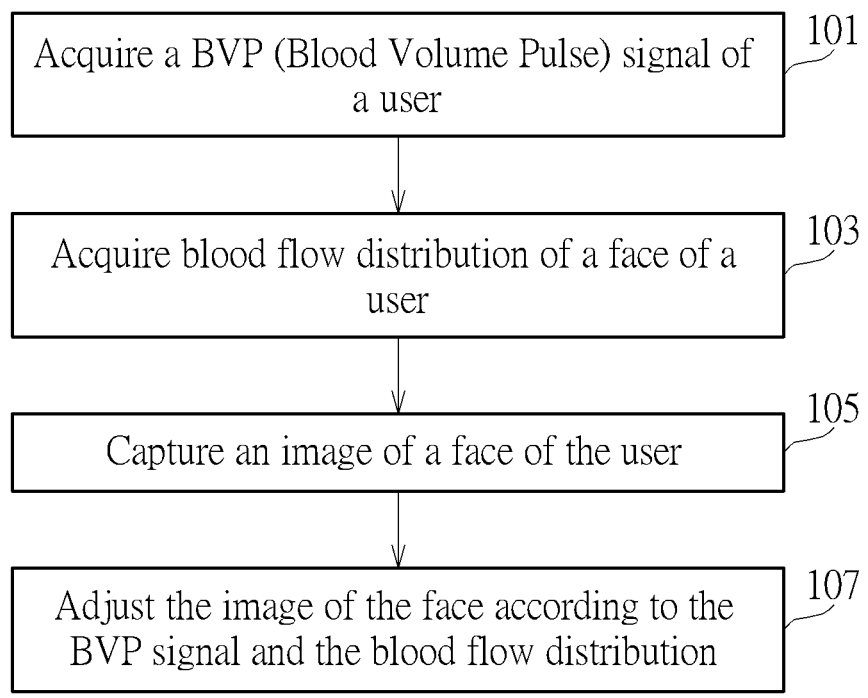
FIG. 1 is a flow chart illustrating a portrait image processing method according to one embodiment of the present invention.

FIG. 1 is a flow chart illustrating a portrait image processing method according to one embodiment of the present invention. Please note, the sequence of steps of the portrait image processing method is not limited to the sequence shown in FIG. 1.

FIG. 1 comprises following steps:

Step 101

Acquire a BVP (Blood Volume Pulse) signal of a user.

Step 103

Acquire blood flow distribution of a face of a user.

Many methods can be applied to acquire blood flow distribution. For example, a U.S. Pat. No. 7,267,651 discloses such technique. However, the step 103 is not limited to be implemented by such method. The blood flow distribution can be pre-recorded in a storage device and read out when needed.

Step 105

Capture an image of a face of the user.

Step 107

Adjust the image of the face according to the BVP signal and the blood flow distribution.

As above-mentioned, the faces illustrated in steps 105, 107 can be replaced by any other specific portion of a user.

In one embodiment, the step 107 synthesizes the BVP signal to the image of the face according to the blood flow distribution. For example, the step 107 synthesizes the BVP signal to the image of the face according responses of the BVP signal and at least one signal in an R channel, a G channel and a B channel. For example, the step 107 synthesizes the BVP signal to the image of the face according responses of the BVP signal and responses of signals in the R channel for the used camera. For another example, the step

107 synthesizes the BVP signal to the image of the face according responses of the BVP signal for the used camera and responses of signals in the R channel and the G channel for the used camera.

In one embodiment, the step 107 synthesizes the BVP signal to the image of the face via following Equation (1):

$$\Delta C(x,y,t)=W*F(x,y)*BVP(t) \qquad \text{Equation (1):}$$

W is a weight for the BVP signal for one of the R channel, the G channel and the B channel, the F(x,y) is the above-mentioned blood flow distribution and BVP(t) is the BVP signal. For different channels, the weight W may be different. In one embodiment, after synthesizing the BVP signal to the image of the face according to the blood flow distribution, the skins of the user in the adjusted image can have a better brightness, a better smoothness or a better rosy level.

Figure 2:
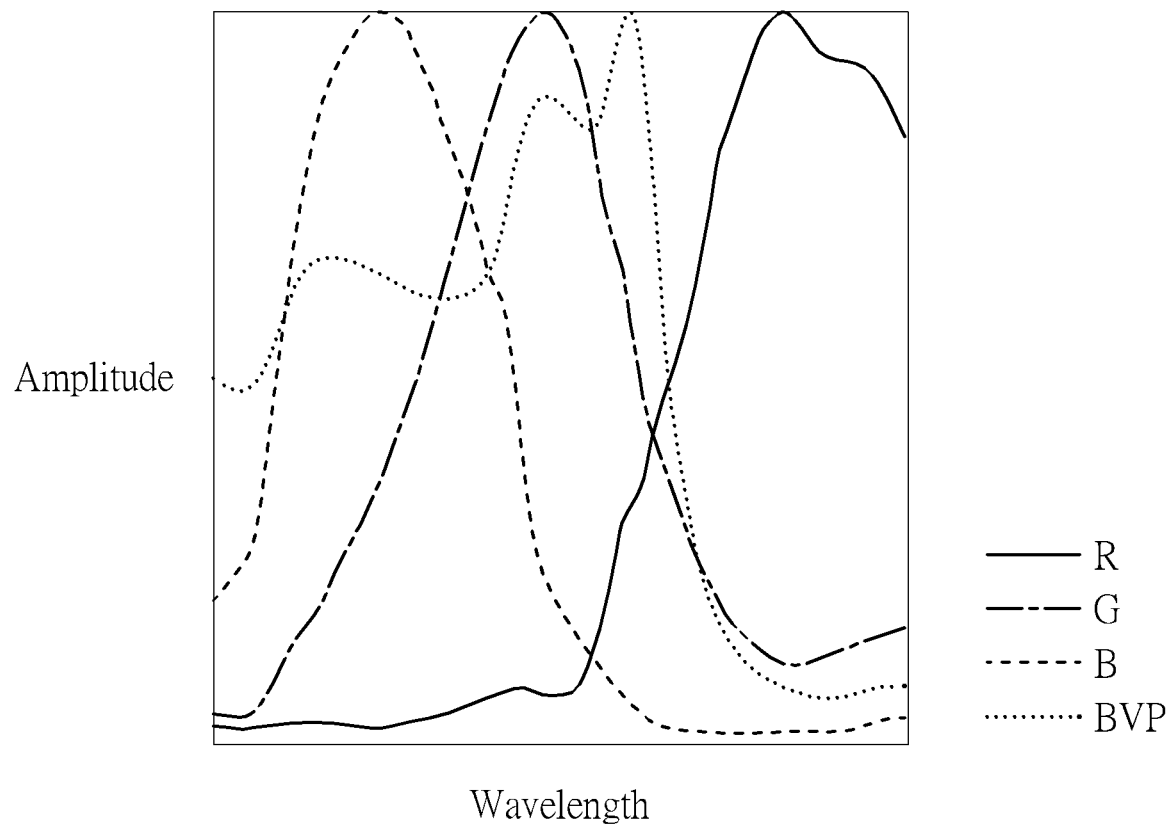
FIG. 2 is a schematic diagram illustrating the responses of RGB signals and the BVP signal.

FIG. 2 is a schematic diagram illustrating the responses of RGB signals and the BVP signal for the used camera, which is from a paper "Wenjin Wang et al., 2017, Amplitude-selective filtering for remote-PPG". Since FIG. 2 illustrates responses for the BVP signal and responses for the signals in the R channel, the G channel and the B channel (i.e., RGB signals), the weights for different channels can be set based on the responses illustrated in FIG. 2. However, please note the responses may change for different cameras (i.e., different image sensors), thus the scope of the present invention is not limited to be implemented by the relations disclosed in FIG. 2.

Figure 3:
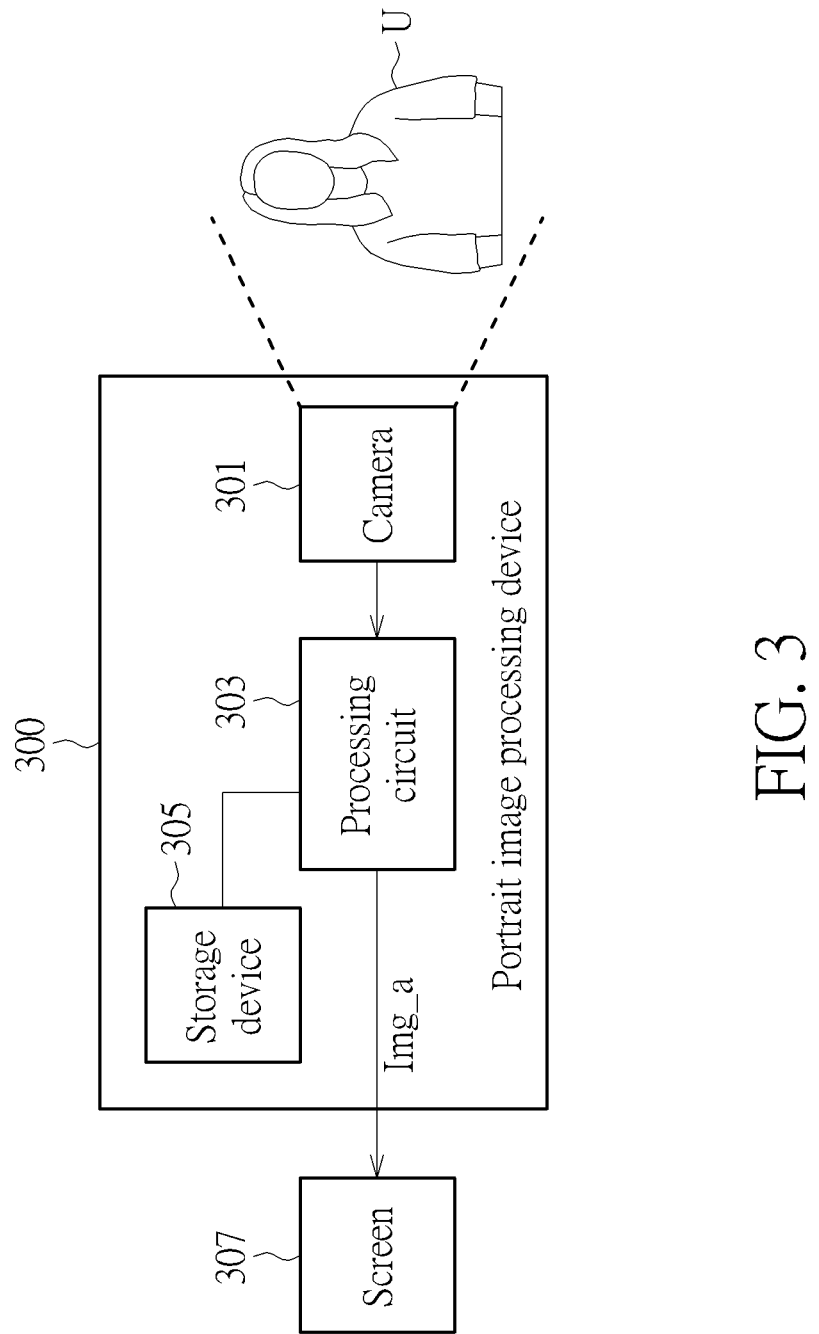
FIG. 3 and FIG. 4 are block diagrams illustrating portrait image processing devices according to different embodiments of the present invention.
Figure 4:
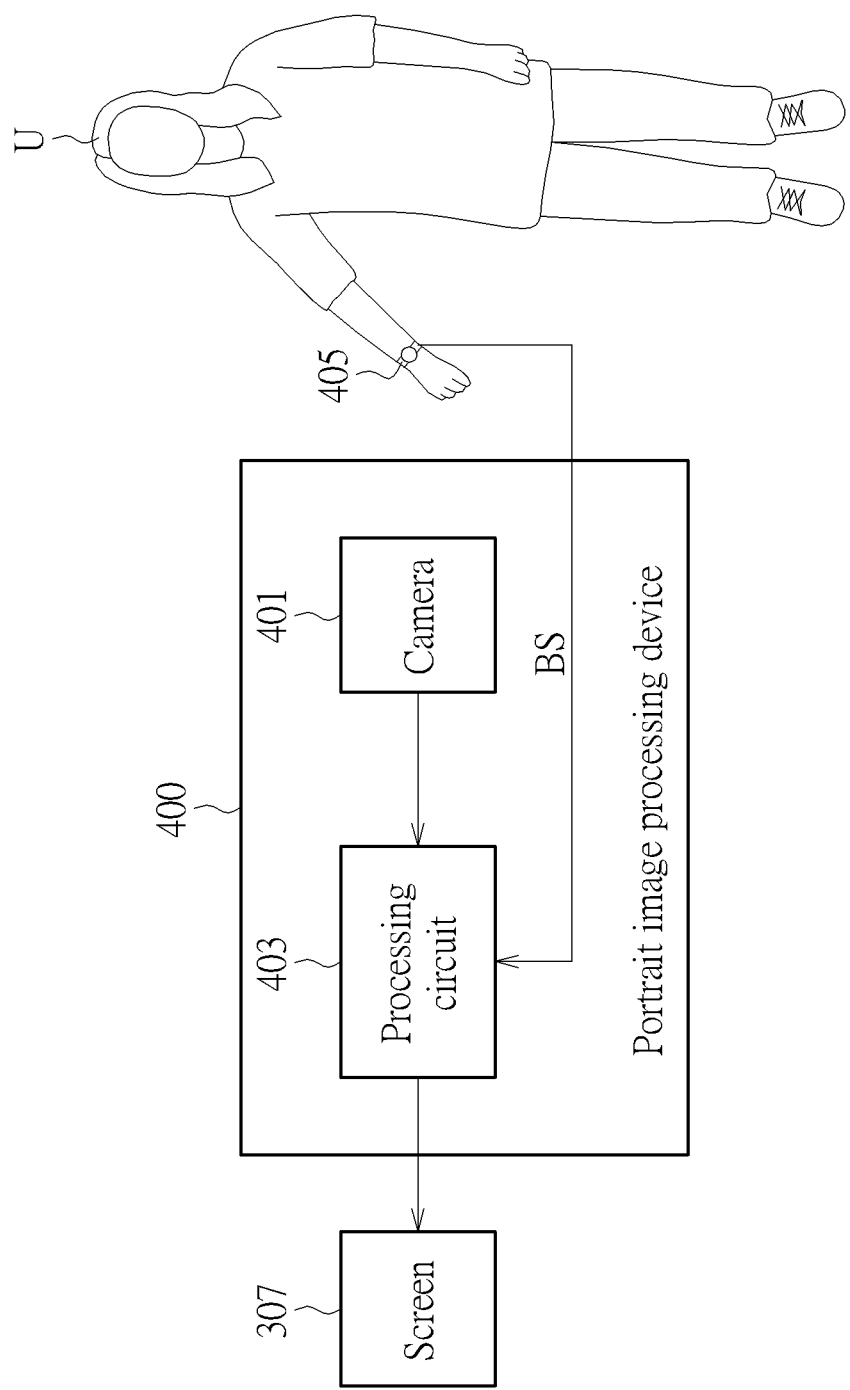

The above-mentioned portrait image processing method can be implemented by various devices. FIG. 3 and FIG. 4 are block diagrams illustrating portrait image processing devices according to different embodiments of the present invention. In the embodiment of FIG. 3, the portrait image processing device 300 comprises a camera 301 and a processing circuit 303. The camera 301 is configured to capture an image of a face of a user. The processing circuit 303 is configured to perform following steps: acquiring a BVP signal of the user; acquiring blood flow distribution of the face; and adjusting the image of the face according to the BVP signal and the blood flow distribution. These steps are the steps illustrated in FIG. 1. It will be appreciated that the processing circuit 303 can be separated into more components for performing different functions.

In one embodiment, the camera 301 further captures an image of a hand or a neck of the user, and the processing circuit 303 acquires the BVP signal according to the image of the hand or the neck. However, the BVP signal can also be acquired by images of other portions of the user. Also, in one embodiment, the portrait image processing device 300 further comprises a storage device 305, which is configured to prerecord face blood flow distribution of the face of the user, which can be measured by the above-mentioned conventional method. The processing circuit 303 reads the face blood flow distribution from the storage device when the user uses the portrait image processing device 300. Please note, the storage device 305 can be provided outside the portrait image processing device 300 rather than limited to be inside the portrait image processing device 300.

In another embodiment, the storage device 305 is configured to prerecord a standard face blood flow distribution, which means a predetermined face blood flow distribution for reference. The processing circuit 303 maps the standard face blood flow distribution to face blood flow distribution of the face of the user according to the image of the face. For example, the processing circuit 303 can map the standard face blood flow distribution to face blood flow distribution according to features of the image of the face, such as the distance between two eyes, the width of the face or a width of the forehead. After the portrait image captured by the camera 301 is adjusted by the processing circuit 303 to generate an adjusted portrait image Img_a, the processing circuit 303 outputs the adjusted portrait image Img_a to a screen 307. Afterwards, the adjusted portrait image Img_a is displayed on the screen 307.

In the embodiment of FIG. 4, the portrait image processing device 400 also comprises a camera 401 and a processing circuit 403. The camera 401 is also configured to capture an image of a face of a user. However, in the embodiment of FIG. 4, the processing circuit 403 acquires the BVP signal BS from a PPG (photoplethysmography) sensor 405 rather than acquiring the BVP signal from an image captured by the camera 401. In one embodiment, the PPG sensor 405 is a wearable device worn by the user U, such as a smart watch or a smart wristband. Other details of the image processing device 400 are illustrated in the embodiment of FIG. 3, thus are omitted for brevity here.

Figure 5:
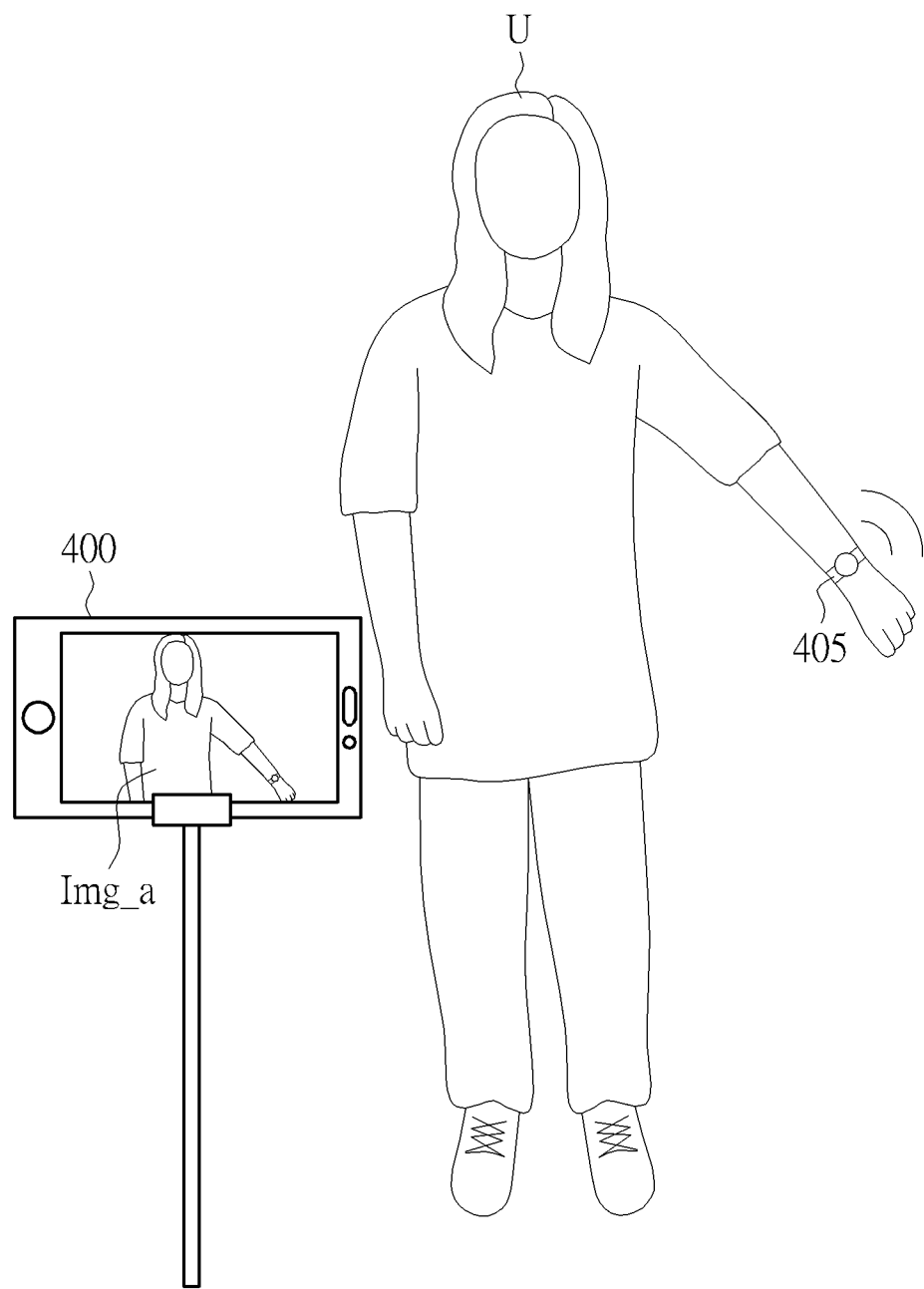
FIG. 5, FIG. 6, FIG. 7 and FIG. 8 are examples of applications of the portrait image processing method provided by the present invention.
Figure 6:
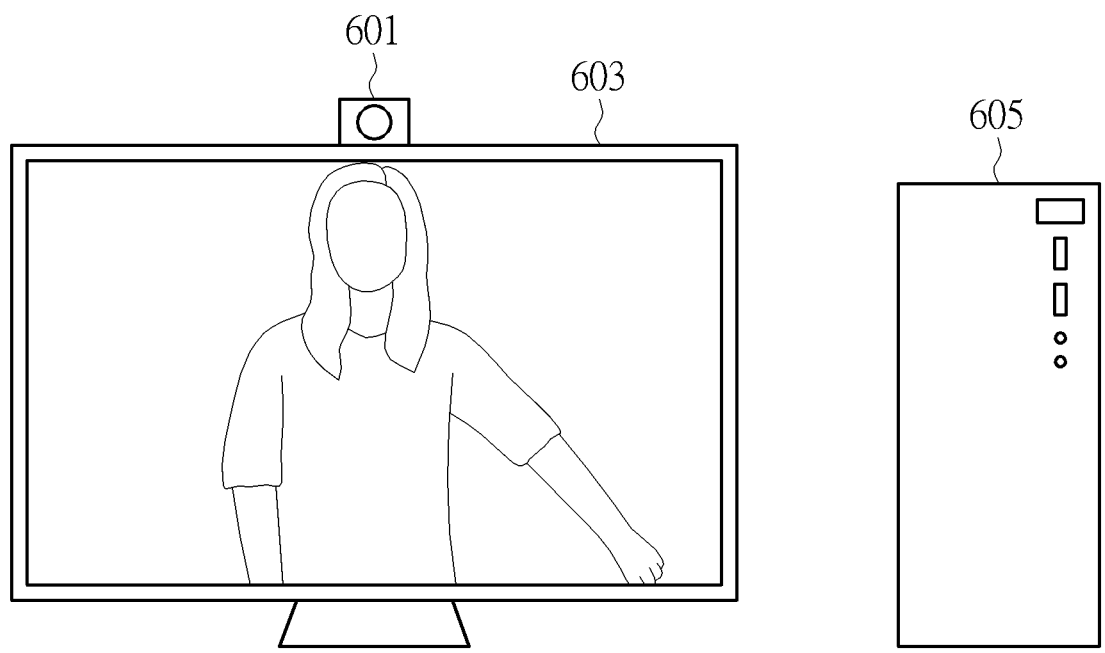

The preceding examples can be used in a variety of situations. FIG. 5, FIG. 6, FIG. 7 and FIG. 8 are examples of applications of the portrait image processing method provided by the present invention. The example illustrated in FIG. 5 corresponds to the embodiment illustrated in FIG. 4. In the embodiment of FIG. 5, the portrait image processing device 400 is a mobile phone. Also, the user U wears the PPG sensor 405 for transmitting BVP signals to the portrait image processing device 400. In such case, the user U uses the camera of the portrait image processing device 400 to perform live broadcast or record videos, and the audiences thereof receive the images which have been processed by the above-mentioned portrait image processing method (i.e., the adjusted image Img_a).

The above-mentioned cameras 301,401, the processing circuits 303, 403 and the screen 307 are not limited to be provided in a single device. For example, in the embodiment of FIG. 6, which corresponds to the embodiment illustrated in FIG. 3, the user U uses the camera 601 above the screen 603 to capture an image thereof, uses the processing circuit (e.g., a micro-processor) in the computer case 605 to acquire BVP signal according to the image captured by the camera 601, and uses the processing circuit in the computer case 605 to adjust the image captured by the camera 601.

Figure 7:
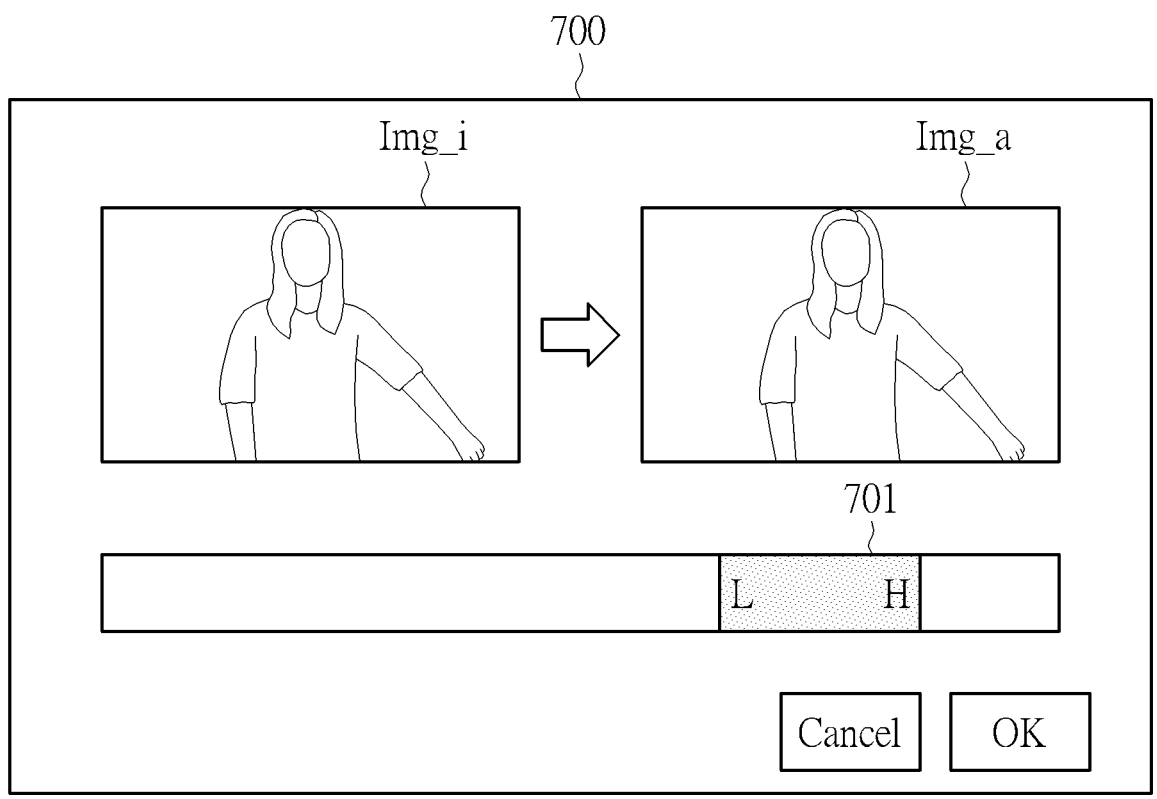

In one embodiment, a user interface is further displayed on the screen 307. The user interface is for adjusting a synthesizing level which means a level that the BVP signal is synthesized to the image of the face. As illustrated in the embodiment of FIG. 7, a user interface 700 is displayed on the screen 307 in FIG. 3. Also, a control bar 701 is provided in the user interface 700. If the control bar 701 is moved more left, the adjusted image Img_a is more similar with the initial image Img_i which is the image captured by the camera 301 and not adjusted. On the opposite, if the control bar is moved further to the right, the initial image Img_i is further adjusted according to the BVP signal and the blood flow distribution to generate the adjusted image Img_a.

Figure 8:
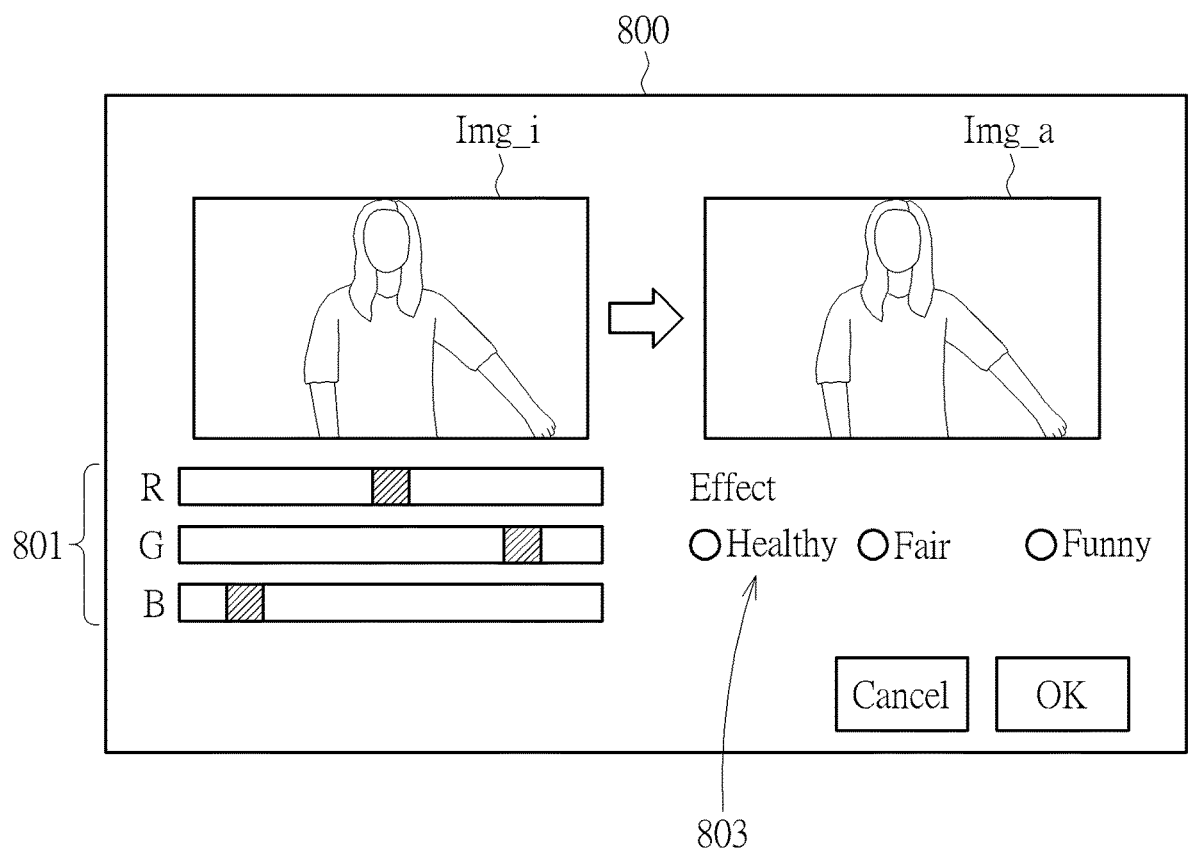

Besides the control bar 701 illustrated in FIG. 7, the user interface can comprise more control commands. In the embodiment of FIG. 8, the user interface 800 comprises control regions 801 and 803. The control region 801 can be used for adjusting the component of signals in R channel, G channel and B channel in the adjusted image Img_a. That is, the control region 801 can be applied for controlling the weights in the Equation (1). Further, the control region 803 can be applied to control the effect which the user wants to show on the adjusted image Img_a. For example, if the user selects "healthy" effect, the user's face may become rosy-cheeked or bronze. Further, if the user selects "fair" effect, the user may have a fait skin. Besides, if the user selects "funny" effect, some special effects may be provided in the adjusted image Img_a based on the BVP signal. For example, if the BVP signal means that the user has a high heart rate, it may mean the user is angry or excited, thus fire effect or glow effect may be added to the adjusted image Img_a.

In view of above-mentioned embodiments, the parameters of the portrait images of the user can be adjusted based on BVP signals, thus the adjusted portrait image may be more realistic or more vivid.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A portrait image processing method, applying to a portrait image processing device, comprising:
    (a) acquiring a BVP (Blood Volume Pulse) signal of a user;
    (b) acquiring blood flow distribution of a specific portion of a user;
    (c) capturing an image of the specific portion; and
    (d) adjusting the image of the specific portion according to the BVP signal and the blood flow distribution;
    wherein the image processing method further comprises:
    displaying a user interface on a screen;
    adjusting a synthesizing level, which means a level that the BVP signal is synthesized to the image of the specific portion according to the blood flow distribution, via the user interface.

2. The portrait image processing method of claim 1, wherein the step (d) synthesizes the BVP signal to the image of the specific portion according responses of the BVP signal and responses for signals in at least one of a R channel, a G channel and a B channel.

3. The portrait image processing method of claim 2, wherein the step (d) synthesizes the BVP signal to the image of the specific portion via a following equation:

$$\Delta C(x,y,t)=W*F(x,y)*BVP(t)$$

wherein W is a weight for the BVP signal for one of the R channel, the G channel and the B channel, the F(x,y) is the blood flow distribution and BVP(t) is the BVP signal.

4. The portrait image processing method of claim 1, wherein the specific portion is a face of the user.

5. The portrait image processing method of claim 4, wherein the step (a) captures an image of a hand or a neck of the user, and the step (a) acquires the BVP signal according to the image of the hand or the neck of the user.

6. The portrait image processing method of claim 4, wherein the step (a) senses the BVP signal via a wearable device worn by the user.

7. The portrait image processing method of claim 4, further comprising:
    prerecording face blood flow distribution of the face of the user in a storage device;
    reading the face blood flow distribution from the storage device when the user uses the portrait image processing device.

8. The portrait image processing method of claim 4, further comprising:
    prerecording standard face blood flow distribution in a storage device;
    mapping the standard face blood flow distribution to face blood flow distribution of the face of the user according to the image of the face.

9. A portrait image processing device, comprising:
    a camera, configured to capture an image of a specific portion of a user; and
    a processing circuit;
    wherein the processing circuit is configured to perform following steps:
    (a) acquiring a BVP (Blood Volume Pulse) signal of the user;
    (b) acquiring blood flow distribution of the specific portion; and
    (c) adjusting the image of the specific portion according to the BVP signal and the blood flow distribution;
    wherein the portrait image processing device further comprises a screen;
    wherein the processing circuit is further configured to control the screen to display a user interface;
    wherein the user interface is for adjusting a synthesizing level, which means a level that the BVP signal is synthesized to the image of the specific portion according to the blood flow distribution.

10. The portrait image processing device of claim 9, wherein the step (c) synthesizes the BVP signal to the image of the specific portion according responses of the BVP signal and responses for signals in at least one of a R channel, a G channel and a B channel.

11. The portrait image processing device of claim 10, wherein the step (c) synthesizes the BVP signal to the image of the specific portion via a following equation:

$$\Delta C(x,y,t)=W*F(x,y)*BVP(t)$$

wherein W is a weight for the BVP signal for one of the R channel, the G channel and the B channel, the F(x,y) is the blood flow distribution and BVP(t) is the BVP signal.

12. The portrait image processing device of claim 9, wherein the specific portion is a face of the user.

13. The portrait image processing device of claim 12, wherein the camera captures an image of a hand or a neck of the user, and the step (a) acquires the BVP signal according to the image of the hand or the neck of the user.

14. The portrait image processing device of claim 12, wherein the step (a) senses the BVP signal via a wearable device worn by the user.

15. The portrait image processing device of claim 12, further comprising:
    a storage device, configured to prerecord face blood flow distribution of the face of the user;
    wherein the processing circuit reads the face blood flow distribution from the storage device when the user uses the portrait image processing device.

16. The portrait image processing device of claim 12, further comprising:
    a storage device, configured to prerecord standard face blood flow distribution;
    wherein the processing circuit maps the standard face blood flow distribution to face blood flow distribution of the face of the user according to the image of the face.

* * * * *